(12) United States Patent
Marra (10) Patent No.: US 8,607,616 B2
(45) Date of Patent: Dec. 17, 2013

(54) SENSOR FOR SENSING AIRBORNE PARTICLES

(75) Inventor: Johannes Marra, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 308 days.

(21) Appl. No.: 13/127,793

(22) PCT Filed: Nov. 20, 2009

(86) PCT No.: PCT/IB2009/055199
§ 371 (c)(1),
(2), (4) Date: May 5, 2011

(87) PCT Pub. No.: WO2010/061327
PCT Pub. Date: Jun. 3, 2010

(65) Prior Publication Data
US 2011/0216317 A1   Sep. 8, 2011

(30) Foreign Application Priority Data

Nov. 25, 2008 (EP) .................................. 08169892

(51) Int. Cl.
*G01N 15/06* (2006.01)
(52) U.S. Cl.
USPC ........................................ 73/28.02; 73/28.05
(58) Field of Classification Search
USPC ............ 73/23.33, 23.34, 28.01, 28.02, 28.04, 73/28.05
See application file for complete search history.

(56) References Cited

U.S. PATENT DOCUMENTS

| | | | | | |
|---|---|---|---|---|---|
| 3,763,428 | A | * | 10/1973 | Preist | ........................... 324/71.1 |
| 3,978,397 | A | * | 8/1976 | Burry et al. | ................... 324/469 |
| 4,312,180 | A | * | 1/1982 | Reif et al. | .................. 60/39.091 |
| 4,643,745 | A | | 2/1987 | Sakakibara | |
| 4,673,416 | A | | 6/1987 | Sakakibara | |

(Continued)

FOREIGN PATENT DOCUMENTS

| FR | 2715227 A1 | 1/1994 |
|---|---|---|
| GB | 2374671 A | 10/2002 |

(Continued)

OTHER PUBLICATIONS

Chen et al., "A high efficiency, high throughput unipolar aersol charger for nanoparticles", Journal of Nanoparticles Research, 1999.*

(Continued)

*Primary Examiner* — David A Rogers
(74) *Attorney, Agent, or Firm* — Larry Liberchuk (57) ABSTRACT

A particle sensor is disclosed capable of sensing airborne particles larger than about 10 nm in an airflow passing through a passage inside the sensor. The sensor comprises a high-voltage discharge electrode for generating airborne unipolar ions that charge the airborne particles in the airflow. The generated ions are furthermore used to set-up an ionic wind between the discharge electrode and a counter electrode inside the sensor. The ionic wind is the driving force for maintaining the airflow through the sensor and allows sensor operation to occur free of audible noise. The presence of charged particles in the airflow is measured by an electrical current meter in the particle sensing section which measures the particle-bound charge that precipitates per unit time on the surface of a precipitation electrode after all airborne ions have been removed from air by a separate screening electrode positioned upstream of the particle sensing section.

15 Claims, 5 Drawing Sheets

(56) References Cited

U.S. PATENT DOCUMENTS

| | | | |
|---|---|---|---|
| 4,689,056 A | 8/1987 | Noguchi | |
| 4,938,592 A | 7/1990 | Poole | |
| 5,606,112 A | 2/1997 | Flagan | |
| 5,679,907 A | 10/1997 | Ruck | |
| 7,243,560 B2* | 7/2007 | Coyle et al. | 73/863.22 |
| 7,416,902 B2* | 8/2008 | Pletcher et al. | 436/174 |
| 7,437,908 B2* | 10/2008 | Bae et al. | 73/28.02 |
| 7,472,612 B2* | 1/2009 | Zaromb et al. | 73/863.21 |
| 7,549,318 B2* | 6/2009 | Burtscher et al. | 73/28.02 |
| 7,836,751 B2* | 11/2010 | Marra | 73/28.02 |
| 7,997,119 B2* | 8/2011 | Wu | 73/31.03 |
| 8,176,768 B2* | 5/2012 | Kondo et al. | 73/23.33 |
| 8,181,505 B2* | 5/2012 | Mertler et al. | 73/31.03 |
| 2005/0050968 A1* | 3/2005 | Trenholm | 73/865.5 |
| 2005/0160792 A1* | 7/2005 | Booker | 73/28.01 |
| 2005/0193803 A1* | 9/2005 | Carlson et al. | 73/28.02 |
| 2005/0214180 A1 | 9/2005 | Joannou | |
| 2006/0032376 A1 | 2/2006 | Osada | |
| 2008/0041138 A1 | 2/2008 | Marra | |

FOREIGN PATENT DOCUMENTS

| | | |
|---|---|---|
| JP | 57187048 A | 11/1992 |
| WO | WO0038512 A1 | 7/2000 |
| WO | WO2007000710 A2 | 1/2007 |
| WO | WO2008129039 A2 | 10/2008 |

OTHER PUBLICATIONS

Lee et al. "Removal of fine and ultrafine particles from indoor air environments by the unipolar ion emission", Atmospheric Environment, 2004.*

* cited by examiner

SENSOR FOR SENSING AIRBORNE PARTICLES

FIELD OF THE INVENTION

The present invention relates to a sensor for sensing airborne particles larger than 10 nm. The invention also relates to an air handling system comprising the sensor, and to a method for sensing airborne particles larger than 10 nm.

BACKGROUND OF THE INVENTION

Airborne ultrafine particles (UFPs) are particles with a diameter in the range approximately from 10 to 500 nm. In the technical literature, the term UFP is sometimes also used for particles with a diameter below 300 nm. Because inhalation of UFPs is known to be harmful to human health, UFP sensors may be used for monitoring the quality of air, in particular the UFP pollution level in the air, both in the indoor and outdoor environment. Appropriate measures to reduce exposure to airborne UFPs can then be taken when deemed necessary on the basis of the UFP sensor signals. For instance, an air processing system arranged to remove airborne UFPs from the indoor environment can be run more economically when at least the actual indoor UFP concentration level is known. Apart from UFPs smaller than about 500 nm, also airborne fine particles (FPs) sized between about 300 nm and 10 µm are of interest. Even though FPs as a class of particles are believed to be less hazardous than UFPs, any airborne particle smaller than 10 µm can potentially create hazard because it is inhalable and capable of reaching and depositing in the deep alveolar region of the lungs. Thus, also the measurement of airborne FPs along with the measurement of airborne UFPs remains a worthwhile pursuit.

Indoor measurements are preferably performed in premises wherein people live or work, or wherein UFPs are produced, such as cooking areas. To interfere as little as possible with normal human activities, UFP sensors should be small, unobtrusive, and also noiseless. Since the UFP concentration may vary significantly between different rooms, several measurement points are often required within a single residence, and it is therefore desirable to keep the cost per sensor low.

Co-pending patent application WO 2007/000710 relates to a UFP sensor device in which electric precipitation is used to assess the size and concentration of airborne UFPs. A high-voltage discharge electrode is used to generate and emit airborne ions into an airflow entering the device. Part of the airborne ions attach to the UFPs in the airflow, thereby charging them. The charged particles are subsequently captured by a mechanical filter that is disposed in an earthed conducting Faraday cage. The concentration of charged particles can be evaluated by measuring the amount of particle-bound electric charge that deposits inside the mechanical filter. Before reaching the filter, the airflow passes through a parallel-plate precipitation section wherein either or not an electrostatic field can be provided to remove either or not, respectively, part of the charged particles in a certain size range from the airflow by means of electrostatic precipitation. This enables the generation of two different measurement signals, one signal being associated with the measurement of all charged particles in the airflow, the other signal being associated with the measurement of the remaining charged particles in the airflow after part of the charged particles has been removed from the airflow by means of electrostatic precipitation. Combination of the two signals allows both the particle number concentration (as used herein, the particle number concentration is the number of airborne particles in a unit volume of air) and the number-averaged particle diameter to be inferred.

The UFP sensor disclosed in WO 2007/000710 is advantageous for its robust construction wherein the magnitude of the airflow through the sensor is primarily determined by the characteristics of the pump or ventilator drawing air through the sensor and by the pressure drop incurred by the mechanical filter inside the Faraday cage. Small environmental air pressure differences between the air entry and air exit of the sensor do not substantially affect the airflow through the sensor.

There are also known sensors in which an airflow is created by the thermal chimney effect induced by heat that is continuously supplied to air at the bottom end of an open air passage inside the sensor through which the airflow is passing. The thermal energy needed for inducing such an airflow makes operation of the sensor less economical. Moreover, the thermal chimney effect is only effective when the air passage inside the sensor is positioned vertically, thus limiting the general applicability of the thermal chimney effect.

SUMMARY OF THE INVENTION

It is an object of the present invention to provide an improved UFP sensor for use in environments wherein noiseless operation of the sensor is preferred. It is desirable that the components which are active in creating the airflow through the sensor should consume virtually no energy (or at least a reduced amount of energy), be durable, compact, and generate virtually no audible noise (or at least very low audible noise).

In accordance with a first aspect of the present invention there is provided a sensor for sensing airborne particles larger than about 10 nm, such as (preferably) larger than about 20 nm. The sensor comprises a passage with open ends, in which passage the following elements are disposed:

a discharge electrode for generating airborne unipolar ions;

an air-pervious counter electrode adapted to attract the airborne ions;

an air-pervious screening electrode located downstream of the counter electrode; and a particle sensing section for sensing electrically charged airborne particles. The particle sensing section is located downstream of the screening electrode.

The counter electrode is located downstream of the discharge electrode, so that it exerts an attractive force on the airborne ions substantially in the downstream direction. The ions expelled by the discharge electrode and attracted towards the counter electrode will, through the viscous drag they experience when moving through air, accomplish a net air movement in the direction of the counter electrode. This net air movement results in an airflow in the passage which is commonly referred to as the ionic wind. Part of the airborne unipolar ions adsorbs onto airborne particles in the airflow, thereby charging the particles. Many airborne ions are subsequently removed from the air by adsorption on the counter electrode.

Any remaining airborne ions are removed from the airflow by a screening electrode arranged downstream of the counter electrode, so that no airborne ions, or at least a limited number of airborne ions, can enter the particle sensing section. By means of the screening electrode, an electric field is created such that airborne ions are subjected to an electrostatic force moving them out of the airflow. Hence, the electrostatic force applied by the screening electrode on the airborne ions is in a second direction distinct from the downstream direction, in which the airflow moves. Thus, air entering the particle sensing section will contain only charged airborne particles and no airborne ions, or at least a limited number of airborne ions.

A skilled person will appreciate that the discharge electrode, as well as the counter electrode, serves at least two purposes in this embodiment. During operation of the sensor, the discharge electrode creates airborne ions that will, on the one hand, provide the airborne particles with the electric charge necessary for detecting them and, on the other hand, create the ionic wind by transferring momentum to air molecules. The counter electrode is adapted to fulfill the twofold task of subjecting airborne ions to an electrostatic force in the downstream direction and of removing at least part of the airborne ions from the air in its proximity, so that the airborne ions will not perturb the particle detection process by introducing airborne charge not carried by particles into the particle sensing section.

In an advantageous embodiment, the screening electrode subjects the airborne ions to an electrostatic force the direction of which makes an angle with the downstream direction of at least 90 degrees. Preferably, the electrostatic force is directed substantially opposite to the airflow direction. In particular, said second direction may be the upstream direction.

In one embodiment of the invention, the particle sensing section comprises means for subjecting the airflow to an electric field for thereby inducing electrostatic precipitation of at least part of the electrically charged airborne particles on at least one precipitation surface. Electric precipitation represents an advantage over the use of mechanical filters (such as fibrous filters) for capturing particles in that it can be realized at a much lower airflow resistance. This is important since an airflow induced by ionic wind can be established only when the encountered airflow resistance is very small and less than the pressure difference created by the ionic wind, which is typically 5-10 Pa. Suitably, the applied electric field can be made variable in the course of time, so that the particle size regions of the partly and fully precipitating particles can be varied. This can be used to obtain insight in the relative width of the size distribution of the airborne particles. In the present embodiment, the particle sensing section further comprises at least one electric current meter. The at least one current meter is electrically connected to one or more of said at least one precipitation surface, thereby generating a measurement signal indicative of the charge of any electrically charged airborne particles that precipitate on the precipitation surface or surfaces. The measured current represents the particle-bound charge that deposits per unit time on the precipitation surface. Varying the electric field may result in a variation of the amount of precipitated charged particles and thus in a variation of the measured electric current.

In a further embodiment, the means for subjecting the airflow to an electric field comprises at least two conducting electrode elements, which are parallel to each other. At least one of the conducting elements comprises a precipitation surface. The electric field can be created across the airflow conduit between at least two parallel conducting plates that may be configured either in a straight or cylindrical configuration. This means that the field is essentially perpendicular to the conduit and thus to the direction of the passage. The separation of the parallel conducting plates should be sufficiently large in order to not significantly impede the airflow.

Instead of using a parallel-plate electrode assembly inside the particle sensing section for enabling charged-particle precipitation, one could alternatively apply a stack of at least two parallel coarse-mesh metallic gauze electrodes, neighboring gauzes being set at different electric potentials with respect to each other. The plane of the gauze electrodes can be given different orientations with respect to the direction of the airflow through the particle sensing section because the gauzes themselves are air-pervious.

In another embodiment of the present invention, the screening electrode comprises at least two screening electrode elements, which are parallel to one another. The electric field between the screening electrode elements varies in the course of time between a first screening field strength $E_{scr,1}$ and a second screening field strength $E_{scr,2}$. The first screening field strength is determined so that substantially all airborne ions precipitate before leaving the screening electrode (i.e., the field strength is sufficiently high) and so that at most 20% of the electrically charged airborne particles in the airflow precipitate before leaving the screening electrode (i.e., the field strength is sufficiently low). The second screening field strength is higher than the first screening field strength and selected (i.e., sufficiently low) so that a portion of all charged airborne particles having a size larger than a predetermined particle size pass through the screening electrode. Preferably, the first screening field strength is tuned so that only a part as small as possible of the electrically charged particles precipitate. This strategy prevents any airborne ions, or at least the majority of the airborne ions, from entering the particle sensing section. Preferably, the second screening field strength is tuned so that single-charged particles (i.e., particles carrying only one elementary charge) having a size of about 10-20 nm are only partially, preferably for less than 90%, precipitated before leaving the screening electrode. In response to the varying screening field strength, the current $I_s$ measured by the current meter attached to the precipitation electrode, whereupon charged-particle precipitation occurs inside the particle sensing section, also varies in the course of time between a first current value $I_1$ and a second current value $I_2$. The respective current values can be used to characterize the airborne charged particles in terms of their number concentration and their number-averaged particle size.

In an advantageous embodiment of the invention, the sensor further comprises an optical particle detection unit capable of optically detecting airborne particles in the airflow. Airborne particles can be easily detected only when they are larger than about 300 nm. With a suitably configured optical particle detection unit, it is even possible to distinguish several size classes of particles in the 300 nm-10 μm particle size interval. The addition of an optical particle detection unit to the sensor enables not only the sensing of ultrafine particles in the 10-300 nm size range but also the sensing of fine particles larger than 300 nm. This is beneficial because any presence of airborne particles smaller than 10 μm can be hazardous in view of their ability to be inhaled and deposit deep in the respiratory tract. Airborne particles larger than 300 nm cannot easily be detected via a measurement of their charge because the contribution of the particle charge associated with particles larger than 300 nm to the total particle charge sensed by the particle sensing section is usually negligible when compared with the particle charge associated with airborne particles smaller than 300 nm. At the same time, airborne particles larger than 300 nm are easier detected by optical means than particles smaller than 300 nm. Hence, the information obtained with the optical particle detection unit, which may be provided to an evaluation unit as a measurement signal, complements the information obtained with the charged-particle sensing section. The optical particle detection unit is preferably arranged upstream from the discharge electrode to avoid any charged-particle precipitation inside the optical particle detection unit.

In one embodiment of the invention, the potentially health-hazardous ozone, which is produced by the discharge electrode, is removed from the airflow before it leaves the sensor. This can be achieved by passing the airflow along a surface and/or through a porous medium, capable of absorbing or decomposing ozone. For this purpose, the surface and/or porous medium can be provided with activated carbon.

In a further embodiment of the invention, there is provided an evaluation unit capable of receiving the measurement signal(s) from the electric current meter connected to the precipitation surface and, if the sensor comprises an optical particle detection unit, from the optical particle detection unit. If the particle-sensing section is subdivided into a sequence of subsections with separate current meters, then preferably all the measured electric currents are provided as input signals to the evaluation unit. The evaluation unit is adapted to output a signal indicative of at least one of:

a length concentration of airborne particles larger than 10 nm, such as larger than 20 nm, in the airflow;

a number concentration of airborne particles with a diameter larger than 10 nm, such as larger than 20 nm, in the airflow;

a number-averaged particle size of airborne particles larger than 10 nm, such as larger than 20 nm, in the airflow; and a concentration of optically-detected airborne particles in the airflow.

Further, the evaluation unit may relate its output data to one of more of the voltage settings inside the sensor or to the created process conditions inside the sensor, notably the magnitude of the airflow through the passage.

In yet another embodiment of the invention, the sensor is operable in a calibration mode, which preferably corresponds to operating all components as described above except for the discharge electrode, which is deactivated. In this mode, normally no airborne ions are generated by the discharge electrode. If no airborne ions are generated, no ionic wind-induced airflow is created through the passage inside the sensor and also no particle charging or charged-particle precipitation can occur. The resulting measured signal of the current meter measuring the current induced by the precipitating charged particles inside the particle sensing section can be used as the bias signal defining its zero reading. Preferably, the sensor is periodically operated in calibration mode to periodically check whether the zero reading of the current meter is correct and, if necessary, to make adjustments to the current meter readings when drifts in the bias signal are observed over time.

In another advantageous embodiment of the invention, the evaluation unit is capable of generating a cumulative number from its output data in the course of time. Preferably, number cumulation starts from zero after having serviced the sensor, the sensor servicing involving at least a cleaning of the airflow passage inside the sensor from deposited particles. The cumulative number can be proportional to an approximate total amount of UFPs that has precipitated inside the particle sensing section since the last sensor servicing or to an approximate total amount of optically detected particles that has passed the optical detection unit since the last sensor servicing. It could also be a linear combination of these numbers. As such, the cumulative number approximately reflects the magnitude of at least part of the total amount of deposited material inside the sensor. When the cumulative number exceeds a set maximum value, the evaluation unit is arranged to generate a warning message that a sensor servicing is recommended. A timely sensor servicing is beneficial to warrant a reliable and predictable sensor operation and functionality. After a sensor servicing, the cumulative number is reset to zero.

In a further advantageous embodiment of the invention, one or both ends of the passage is shielded from direct exposure to the environment by a shielding plate facing the aperture. This measure prevents that the ionic wind-induced airflow through the passage inside the sensor becomes readily affected by air movements induced by spatial air pressure gradients in the environment wherein the sensor is present. This enhances the reliability of the sensor measurements and prevents interference by environmental conditions.

In accordance with a second aspect of the invention, there is provided an air handling system, whose settings are controllable on the basis of an output signal provided by at least one sensor for sensing airborne particles according to the invention forming part of the system. The sensor or sensors may be located in the space serviced by the air handling system or outside of it, such as outdoors, from where fresh air is fetched. In addition to the particle sensor, the air handling system may comprise means for air cleaning on demand and/or for air conditioning on demand and/or for air ventilation on demand, thereby decreasing the indoor concentration of airborne particles if this concentration exceeds a predetermined value in the premises served by the air handling system. In the particular case of an air handling system for a car cabin, the system may compare the indoor and outdoor concentrations of airborne particles in order to determine an appropriate rate of internal air re-circulation and of air exchange with the outside environment.

In accordance with a third aspect of the invention, there is provided a method of sensing airborne particles larger than 10 nm, such as (preferably) larger than 20 nm. For the purpose of explaining this method, an air sample—or a control volume, i.e., a specific collection of air molecules and airborne particles suspended therein—which is contained in a passage having a first and a second open end, is considered. The method comprises the following consecutive steps:

generating airborne unipolar ions;

applying a first electric field adapted to subject generated airborne ions to an electrostatic force along the passage into a first direction, thereby causing a movement of the air sample in the first direction and charging airborne particles in the air sample;

passing the air sample through an air-pervious counter electrode adapted to remove part of the airborne ions from the air sample;

applying a second electric field adapted to subject remaining airborne ions to an electrostatic force in a second direction, distinct from the first direction, for separating airborne ions from the air sample;

applying a third electric field for precipitating airborne charged particles onto a precipitation surface in the passage; and measuring the charge of the precipitated charged particles on the precipitation surface.

Because some airborne ions will adhere to airborne particles, the presence of unipolar airborne ions causes the airborne particles to become electrically charged. By means of an applied first electric field, the generated airborne ions are moved into a first direction along the passage towards the second end of the passage. The viscous drag experienced by moving ions through the air induces a net airflow into the first direction. The first electric field ends at an air-pervious counter electrode, through which the airflow passes. Many airborne ions are removed from the airflow by the counter electrode. A presence of remaining airborne ions in the airflow may disturb subsequent electrical measurements on charged airborne particles, and for this reason an electric screening field is applied to remove all remaining airborne ions from the sampled airflow. The screening field strength is preferably selected so that substantial precipitation of charged particles from the airflow is not induced (i.e., the field strength is kept sufficiently low). Subsequently, electric charge in the airflow is chiefly carried by airborne particles. The charged airborne particles are then at least partly caused to precipitate onto the surface of a precipitation electrode in the passage under the influence of a second electric field, and the amount of precipitated charge, which is indicative of the concentration of the precipitated charged particles, is measured.

In one embodiment of the invention, precipitation of charged particles is caused by subjecting the sampled airflow to an electrostatic field directed perpendicular to the direction of the airflow through the passage. At a given field strength, small charged particles precipitate relatively more rapidly than larger charged particles. Hence, a variation of the electrostatic field strength, be it in time or space, is useful for extracting information about the size distribution of the airborne particles in the sampled airflow.

In another advantageous embodiment of the inventive method, airborne particles in the sampled airflow are furthermore optically detected by means of an additional optical particle detection unit. This is readily possible for airborne particles larger than about 300 nm, which is advantageous because particles larger than about 300 nm are normally not easily detected by electrical means.

Additional advantageous embodiments of the method include one wherein the step of removing ozone from the sampled airflow in the passage downstream from the location where airborne ions are generated.

These and other aspects of the invention will be apparent from and elucidated with reference to the embodiments described hereinafter.

BRIEF DESCRIPTION OF THE DRAWINGS

Currently preferred embodiments of the present invention will now be described with reference to the appended drawings, of which.

DETAILED DESCRIPTION OF THE EMBODIMENTS

Figure 1:
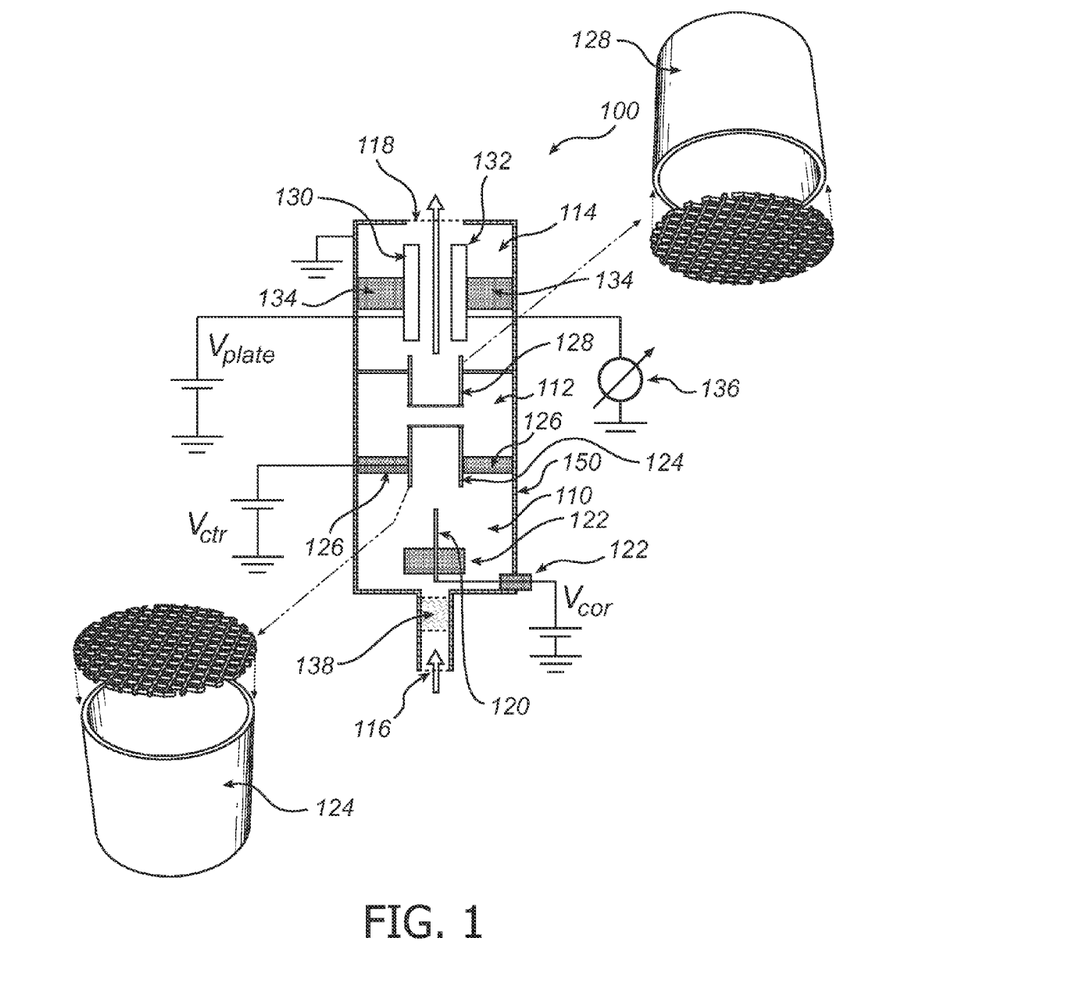
FIG. 1 is a diagrammatic cross-section view of a UFP sensor according to an embodiment of the present invention comprising one current meter.

FIG. 1 shows a UFP sensor 100 according to a particular embodiment of the present invention. The sensor 100 comprises an air-filled central passage comprising three connected sections 110, 112, 114, wherein the first section 110 for charging particles extends in the direction of the passage from an inlet section 116 to a counter electrode 124; the second section 112 extends from the counter electrode 124 to a screening electrode 128; and the third section 114, intended for the sensing of charged particles, extends from the screening electrode 128 to an outlet section 118. The inlet section 116 and outlet section 118 are provided in the form of apertures in a housing 150 of the sensor 100 that is connected to earth or some reference (zero) potential.

In the first section 110, there is provided a high-voltage corona discharge electrode 120, which is connected to a potential $V_{cor}$ and electrically insulated from other portions of the sensor 100 by means of insulator 122. The potential $V_{cor}$ may be variable and regulated such that a constant current of unipolar ions is emitted from the discharge electrode 120. A current in the range of 1-2 µA has been found suitable for many applications. The geometry of the discharge electrode is preferably adapted to promote efficient generation of airborne ions while limiting ozone generation and particle deposition on the discharge electrode. Preferably, a sharp needle-tip electrode is used that is composed of a chemically-inert material such as molybdenum or tungsten. It has been found advantageous, notably for limiting the ozone production, to produce positively-charged airborne ions.

The discharge electrode 120 repels the cloud of airborne ions, and the cloud immediately expands due to repulsion between the ions themselves. A counter electrode 124, to which a potential $V_{ctr}$ is applied, is provided at the downstream end of the first section 110 for attracting ions from the discharge electrode 120 towards the counter electrode 124. The geometry of the counter electrode 124 is preferably determined by at least three requirements:

(i) the counter electrode 124 should draw the ions substantially in the downstream direction of the passage;

(ii) the path of the airborne ions drawn from the discharge electrode 120 to the counter electrode 124 should be such that the paths of all parts of the airflow cross the paths of the ions, so that no airborne particles, or at least a limited portion of the airborne particles, can escape exposure to airborne ions; and (iii) the counter electrode 124 should cause little or no flow resistance.

Indeed, a person skilled in the art will realize that the counter electrode 124 can be suitably realized as a tube with a circular or elliptical opening facing the discharge electrode 120. Most airborne ions will then be attracted towards the circular edge of the open face of the tube facing the discharge electrode 120, thereby being removed from the airflow. The comparatively much smaller electric mobility of the charged particles enables most charged particles to escape precipitation onto the counter electrode 124, allowing them to continue their journey with the airflow through the counter electrode 124. The motion of airborne ions from the discharge electrode 120 towards the counter electrode 124 generates an ionic wind that can create and sustain an airflow through the passage without having to rely on other means for generating airflow, provided that the airflow experiences no more than only a minimal resistance that remains below 5-10 Pa. The contact in the first section 110 between airborne particles and airborne ions results in particle charging according to a physical process commonly referred to as diffusion charging or free-ion charging.

At the downstream end of the second section 112, there is provided a conductive screening electrode 128 set at an electric potential, with respect to the electric potential $V_{ctr}$ on the counter electrode 124, that repels airborne ions from the screening electrode 128 back towards the counter electrode 124. In FIG. 1, the screening electrode is configured as a short open tube having its central axis oriented in the same direction as the central axis of the counter electrode 124. If the electric potential applied to the screening electrode is zero (via a short-circuiting to the earthed sensor housing), $V_{ctr}$ needs to be a negative voltage in order to repel positive ions from the screening electrode 128 back towards the counter electrode 124. By providing the tubular open ends of the counter electrode 124 and of the screening electrode 128 facing each other with parallel-positioned porous gauzes, as shown in FIG. 1, a locally very effective ion screening can be created even at a low screening field strength between the parallel gauzes. Due to the high mobility of airborne ions, the intensity of the electric screening field in the second section 112 can be kept relatively low, so that virtually no precipitation, or at least a very limited amount of precipitation, of charged particles accompanies the ion screening from the airflow.

Downstream of the screening electrode 128, in the third section 114, the airborne charged particles are substantially the only remaining charged bodies in the airflow. The airflow is led through the conduit between two parallel conducting plates 130, 132, of which one 130 is earthed (at potential $V_{earth}$) and the other 132 is maintained at a constant potential $V_{plate}$ to create an approximately homogeneous electric field in a direction perpendicular to the airflow. The plates 130, 132 are electrically insulated from other portions of the sensor 100 by insulators 134. By choosing a sufficiently large value for $V_{plate}$, in relation to the particle charges and particle sizes to be expected and the dimensions of the plates 130, 132, it can be ensured that substantially all airborne charged particles precipitate from the airflow. In the case of positively charged particles and $V_{plate} - V_{earth} > 0$, precipitation occurs on a precipitation surface on the earthed plate 132. The charge carried by precipitating particles on plate 132 is drained to earth via a current meter 136.

Because the charge per particle under conditions of diffusion charging is approximately proportional to the diameter of the particle, the current $I_s$ measured with the current meter 136 is proportional to the length concentration L of airborne particles, i.e., the total length of all lined-up particles per unit air volume, according to:

$$I_s \propto L = \int_{d_p=0}^{\infty} d_p \frac{dN_{UFP}}{d\ln d_p} d\ln d_p \quad (1)$$

If the number-averaged diameter $d_{p,av}$ is known or can be estimated, the particle number concentration N is obtained as $$N = \frac{L}{d_{p,av}} \quad (2)$$

The proportionality factor between $I_S$ and L in equation 1, which depends, inter alia, on the effective degree of charging of the particles, can be determined experimentally or via calibration. Although the integration range in equation 1 extends to infinity, airborne particles larger than 300-500 nm do not normally significantly contribute to L when ordinary ambient air from either the indoor or outdoor environment is concerned. The reason is that their number concentration in air is normally much smaller than the number concentration of particles smaller than 300-500 nm. Thus, L and therefore also N refer in particular to airborne ultrafine particles.

Figure 2:
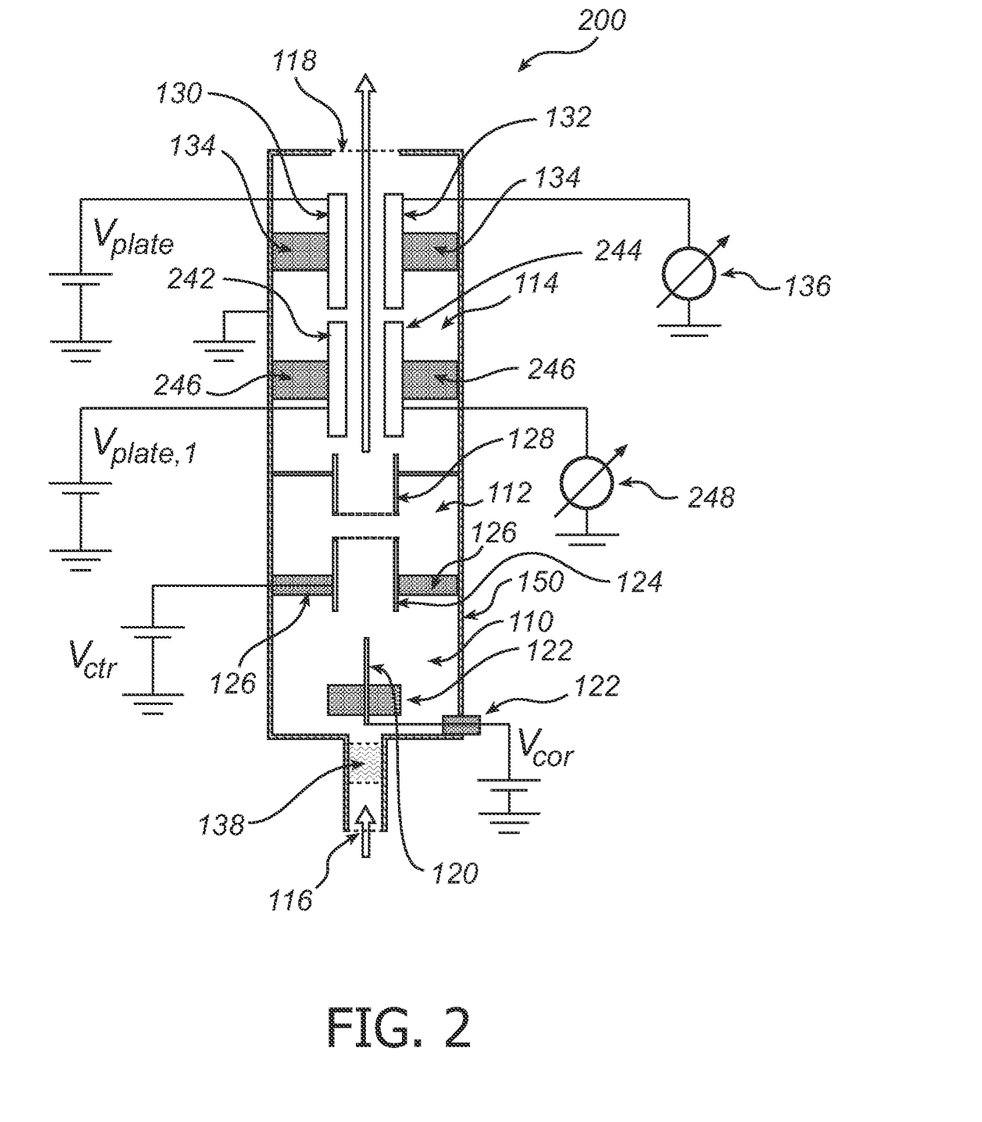
FIG. 2 is a diagrammatic cross-section view of a UFP sensor according to a different embodiment of the invention, in which the particle-sensing section comprises two electric current meters.

An advantageous embodiment of the particle sensor according to the invention is shown in FIG. 2. In a sensor 200, at least one additional pair of conducting plates 242, 244 is provided in the third section 114 via insulators 246. The plate 244 is earthed via a second current meter 248. To the first plate 242, a potential $V_{plate,1}$ applied, while the first plate 130 in the other pair of plates 130, 132 remains set at potential $V_{plate}$. By choosing suitable values of $V_{plate,1}$ and $V_{plate}$, the electric fields created between the two pairs of parallel plates may have different strengths. Preferably, $V_{plate,1}$ is chosen such that only part of the airborne charged particles of any size that contributes to a non-negligible extent to the total particle number concentration is precipitated on plate 244 in the additional pair of plates, thereby giving rise to a first current $I_1$ measured by the connected current meter 248. Preferably, all charged particles larger than 10 nm, more preferably all charged particles larger than 20 nm, are allowed to only partly precipitate from the airflow on plate 244. The remaining airborne charged particles precipitate on plate 132 under the action of a sufficiently strong electric field between the plate elements 130, 132, thereby giving rise to a current $I_2$ measured by the connected current meter 136. It was found experimentally that the particle number concentration N and the average particle diameter $d_{p,av}$ follow from $I_1$ and $I_2$ according to $$N \propto I_1 \quad (3)$$

$$d_{p,av} \propto \frac{I_1 + I_2}{I_1} \quad (4)$$

with proportionality factors that can be determined experimentally or via calibration. The simultaneously measured currents $I_1$ and $I_2$ according to the set-up shown in FIG. 2 allows N and $d_{p,av}$ to be determined under both stationary conditions and transient conditions with respect to the characteristics and concentration of the airborne particles in the airflow.

The airflow through the passage of sensor 200 can be sustained by the ionic wind between the discharge electrode 120 and the counter electrode 124 when the airflow incurs at most only a very low pressure drop across the passage, preferably less than 5-10 Pa.

To further improve the reliability of the current measurements $I_1$ and $I_2$, the UFP sensor is preferably periodically calibrated by reading the current meters 136 and 248 in a state wherein the discharge electrode 120 is inactive and not capable of ion generation, while all other electric potentials are applied as during normal operation. Such a configuration interrupts the generation of the ionic wind, thus stopping the airflow through the passage and the charging of airborne particles, so that the readings of the current meters 136 and 248 should correspond to their zero (base level) readings in the absence of charged-particle precipitation. These zero readings can be subtracted from the readings of subsequent measurements with an activated discharge electrode 120 so that the net current readings correspond with the particle-bound charge that precipitates per unit time on the electrode elements 132 and 244 for precipitation.

In specific embodiments, a sensor according to the present invention may comprise a surface or a porous medium that is provided with a material capable of removing ozone from the airflow. This material may be activated carbon or some other catalytic material and should be present upstream of the air outlet section 118 to prevent ozone escape from the sensor according to the invention. For example, the activated carbon may be applied on the gauzes attached to the counter electrode 124 and the screening electrode 128, respectively, in the sensors shown in FIGS. 1 and 2.

Likewise, it is advantageous to provide a very coarse particle filter 138 near the air inlet section 116 for removing particles with diameters much larger than typical UFP diameters from the airflow before these particles reach the discharge electrode 120. This measure prevents the deposition of large particulate material inside the passage of the sensor, thereby reducing its reliance on periodic sensor servicing (involving a cleaning of the passage), and promoting undisturbed sensor operation.

Figure 3:
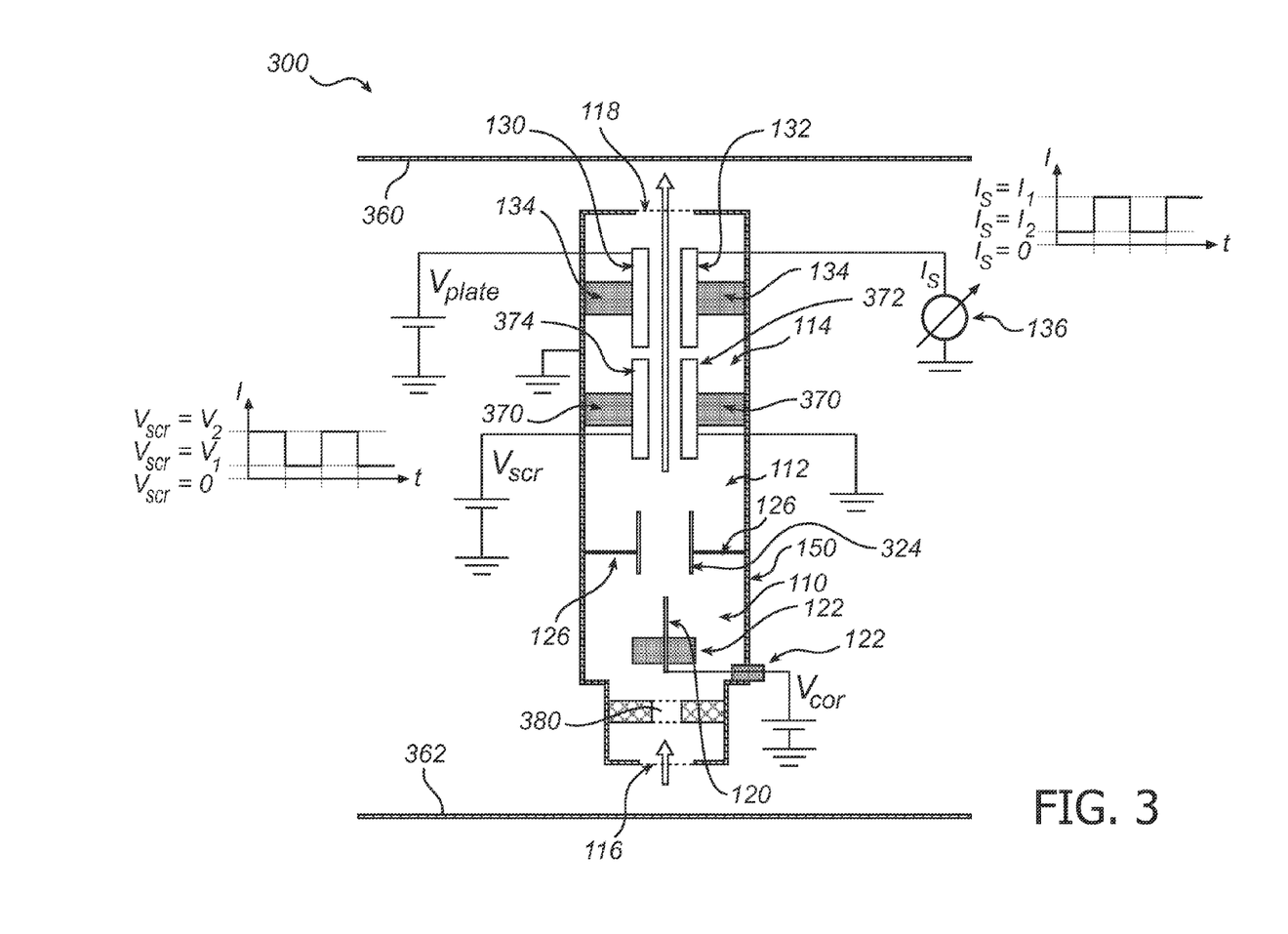
FIG. 3 is a diagrammatic cross-section view of a UFP sensor according to a different embodiment of the invention, in which an optical particle detection unit is arranged upstream from the discharge electrode and wherein the entry and exit sections of the sensor are facing shielding plates.

In another advantageous embodiment of the invention, with reference generally to the schematic drawing in FIG. 3, a particle sensor 300 comprises an air-pervious tubular counter electrode 324 with both tube ends left open, one tube end facing the discharge electrode 120. The counter electrode 324 is preferably electrically short-circuited to the housing 150 of the sensor 300. The second open end of the counter electrode faces the screening electrode 372, 374. The screening electrode is now embodied as a parallel-plate electrode comprising two screening electrode elements 372, 374. A first screening electrode element 374 is connected to the screening voltage supply, and a second screening electrode element 372 is connected to earth potential. The screening voltage supply imposes an electric screening field $E_{scr}$ between the screening electrode elements 372, 374 varying in the course of time between a first screening field strength $E_{scr,1}=V_1/d_{p1}$ and a second screening field strength $E_{scr,2}=V_2/d_{p1}$, with $d_{p1}$ denoting the spacing between the parallel screening electrode elements 372, 374. The first screening field strength $E_{scr,1}$ is selected (sufficiently high) so that remove remaining airborne ions are removed from the airflow but nevertheless does not cause substantial electrostatic precipitation of electrically-charged airborne particles from the airflow (i.e., it is kept sufficiently low). The second screening field strength $E_{scr,2}$ is higher than $E_{scr,1}$ and is capable of precipitating only part of the electrically charged airborne particles from the airflow of any particle size that contributes to a non-negligible extent to the total particle number concentration. Preferably, particles charged with a single elementary charge having a diameter of about 10-20 nm are only partially, for preferably less than 90%, removed from the airflow under the influence of the applied $E_{scr,2}$. The remaining airborne particles reach the particle sensing section. This selection of electrical field strengths also prevents airborne ions from entering the particle sensing section. In response to the varying screening field strength, the current $I_s$ measured by the current meter attached to the precipitation surface whereupon charged-particle precipitation occurs inside the particle sensing section also varies in the course of time between a first current value $I_1$, measured at the first screening field strength $E_{scr,1}$, and a second current value $I_2$, measured at the second screening field strength $E_{scr,2}$. It was experimentally found that the respective current values $I_1$ and $I_2$ can be used to characterize the airborne charged particles in terms of their number concentration N and their number-averaged particle size $d_{p,av}$ according to $$N \propto (I_1 - I_2) \quad (5)$$

$$d_{p,av} \propto \frac{I_1}{I_1 - I_2} \quad (6)$$

The proportionality factors can be determined via calibration. Since airborne charged particles larger than 300-500 nm do not normally significantly contribute to $I_1$ or $I_2$, the data N and $d_{p,av}$ usually refer to airborne ultrafine particles. This can be checked afterwards from the inferred value for $d_{p,av}$.

The sensor in FIG. 3 further comprises an optical particle detection unit positioned upstream from the discharge electrode. The optical particle detection unit is capable of detecting particles larger than 300-500 nm, by irradiating the airflow inside the optical particle detection unit with an incident light beam. Irradiated particles larger than 300-500 nm are capable of scattering light, and the measured characteristics of the scattered light into certain directions away from the direction of the incident beam can be used to infer the approximate amount of airborne particles larger than about 300-500 nm. The combination of an ultrafine particle sensor capable of electrically measuring airborne particles smaller than about 300-500 nm with an optical particle detection unit capable of the optical detection of airborne particles larger than about 300-500 nm is useful to assess and characterize the total amount of potentially hazardous air pollution of inhalable particles smaller than about 10 μm.

In the embodiments of the invention which have been disclosed in FIGS. 1, 2 and 3, numerical operations for returning output values of the sensor—such as the length concentration, the number concentration, the average particle size and the concentration of optically-detectable particles—are performed in respective evaluation units (not shown). An evaluation unit may include computing means but also storage means for constants such as the proportionality coefficients tacitly appearing in equations 1-6. It may receive the input quantities (measurement signals) and output the results as digital or analogue signals.

The sensor in FIG. 3 further comprises a pair of shielding plates 360 and 362 facing the entry section and the exit section of the sensor. A limited spacing is maintained between the shielding plates 360, 362 and the respective aperture in the sensor housing 150. Preferably, the spacing is of the same order of magnitude as the narrowest part of the passage 110, 112, 114. This allows for an unhindered entry and exit of an airflow into and out of the sensor with the magnitude of the airflow determined by the ionic wind existing between the discharge electrode and the counter electrode. At the same time, the shielding plates 360, 362 protect the airflow through the sensor from disturbances by air pressure gradients in the environment around the sensor. This is important because the pressure gradient inside the sensor induced by the ionic wind is only relatively small and can be easily overwhelmed by external influences. The presence of the shielding plates 360, 362 enhances the reliability of the measured sensor signals.

Figure 4:
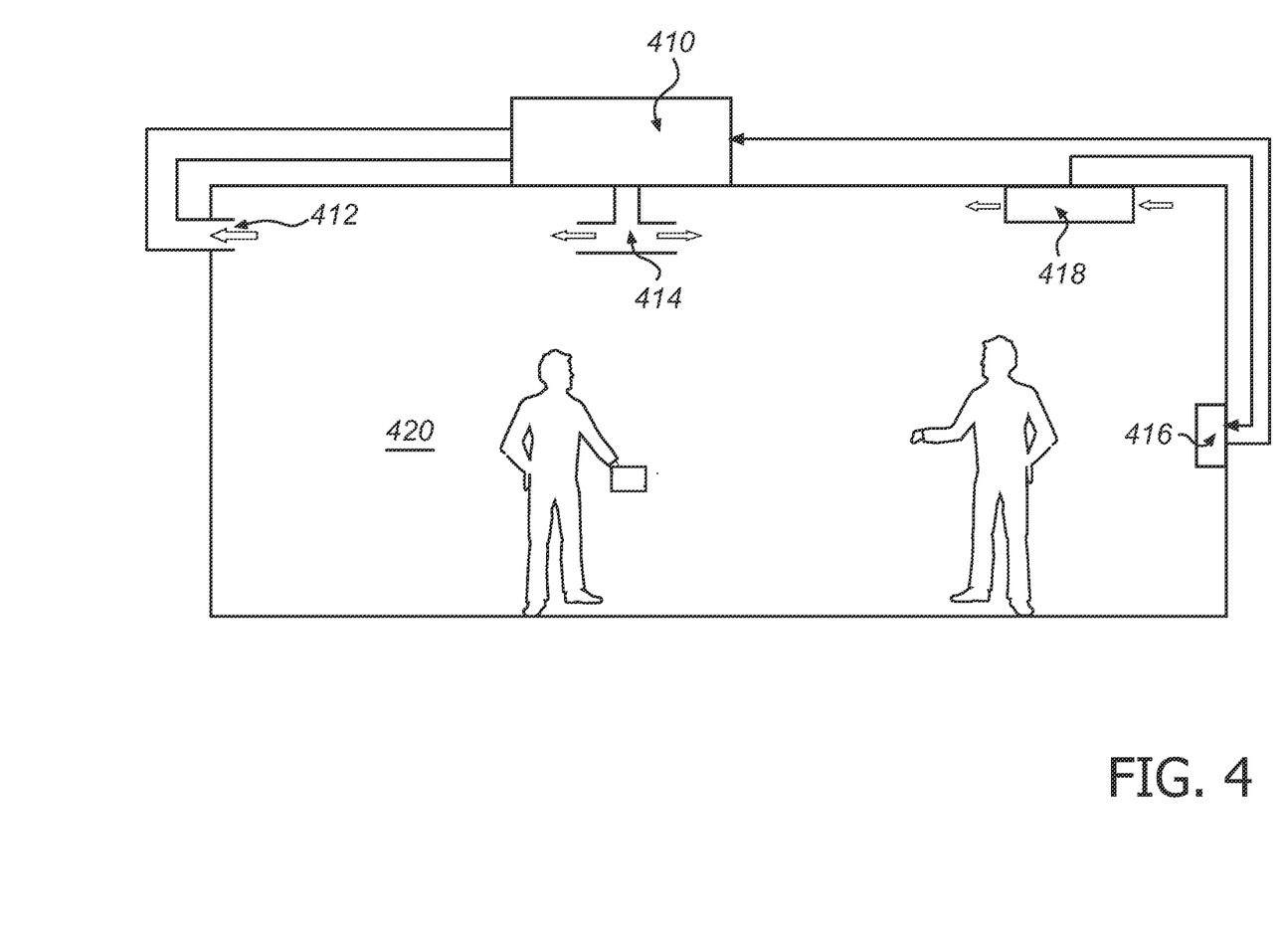
FIG. 4 is a diagrammatic drawing of an air handling system in accordance with a second aspect of the invention.

FIG. 4 shows an air handling system serving a space 420 in which people reside or work. Air is evacuated from the space 420 to an air processing unit 410 via an air outlet 412, and air enters the space 420 via an air inlet 414. A particle sensor 418 according to an embodiment of the present invention generates an output signal indicative of the concentration of airborne particles in the space 420. The output signal is provided to a controller 416, which generates an output signal for the air processing unit 410 on the basis of the output signal from the particle sensor 418. Thus, the operation of the air processing unit 410 is controlled in accordance with the current characteristics of air contained in the space 420.

Figure 5:
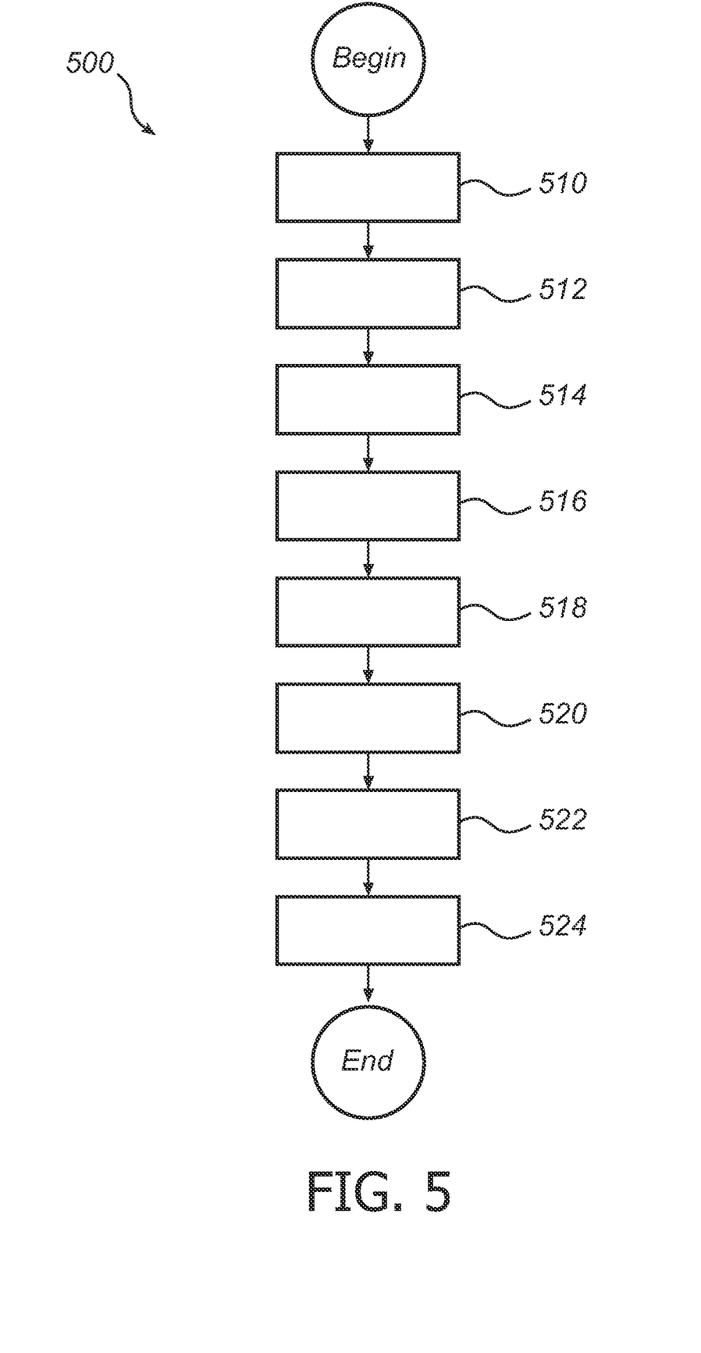
FIG. 5 is a flowchart illustrating a method of sensing UFPs in an air sample in accordance with a third aspect of the invention.

FIG. 5 is a flowchart of a method 500 for sensing airborne particles according to the invention. The method is adapted to sense particles larger than 10 nm, preferably larger than 20 nm, contained in an air sample (control volume) in an open passage for conducting an airflow. As a first step 510, coarser particles in the air sample are detected optically. Since the reliability of optical detectors is usually very sensitive to deposition of particles, this step is preferably performed before any airborne ions have been introduced into the air sample. In a second step 512, airborne ions are generated, which are drawn by an electric field, in step 514, into a first direction parallel to the passage. Due to viscous drag, the air sample and the airborne particles contained therein, is moved in said first direction. Next, in step 516, the air sample is passed through an air-pervious electrode adapted to remove part of the airborne ions from the air sample. The remaining airborne ions, which would otherwise disturb the subsequent measurements, are removed in step 518, wherein the air sample is subjected to a second electric field which subjects the ions to an electrostatic force that moves them in a direction distinct from the first direction, whereby the airborne ions are separated from the air sample. The strength of the second electric field should be so low that the motion of the airborne charged particles, in virtue of their lower mobility and greater inertia, is only affected to a minor or preferably negligible extent. After step 518, the electrically charged particles are substantially the only charged bodies in the air sample, which has a forward net momentum in the first direction. In step 520, the air sample is subjected to a third electric field, which causes the charged airborne particles to precipitate onto a precipitation surface in the passage. In step 522, the charge of the precipitated charged particles on the precipitation surface is measured, whereby the concentration of airborne particles initially contained in the air sample can be characterized. As a variant of steps 520 and 522, the air sample can be subjected to further electric fields. If, for instance, the strengths of the electric fields are different (suitably increasing sequentially) the size distribution of the particles can be derived. In the final step 524, potentially health-hazardous ozone is removed from the sample before it is released into the environment whose particle concentration is being assessed.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the electric field for causing precipitation is generated by one or more pairs of concentric cylindrical plates. Moreover, a sensor according to the present invention could be used for sensing particles in a different size range than stated above.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A sensor (100) for sensing airborne particles larger than 10 nm, comprising a passage (110, 112, 114) with open ends, the passage having disposed in it:
   a discharge electrode (120) for generating airborne unipolar ions in the passage;
   an air-pervious counter electrode (124, 324) adapted to attract said airborne ions;
   an air-pervious screening electrode (128; 372, 374) located downstream of the discharge electrode; and
   a particle sensing section (114) for sensing electrically charged airborne particles in the passage, the particle sensing section being located downstream of the screening electrode, wherein:
   the counter electrode is located downstream of the discharge electrode and upstream of the screening electrode in the passage, thereby being adapted to cause a downstream net flow of airborne ions for thereby generating a downstream airflow; and
   the screening electrode is adapted to subject airborne ions to an electrostatic force in a second direction, distinct from the downstream direction, for separating airborne ions from the airflow.

2. The sensor according to claim 1, wherein the second direction makes an angle of at least 90 degrees with the downstream direction.

3. The sensor according to claim 1, wherein the screening electrode comprises at least two parallel conducting electrode elements (372, 374), the electric field between the screening electrode elements alternating in the course of time between a first screening field strength and a second screening field strength, wherein the first screening field strength is selected so that substantially all airborne ions precipitate before leaving the screening electrode and at most 20% of the electrically charged airborne particles in the airflow precipitate before leaving the screening electrode; and the second screening field strength is higher than the first screening field strength and selected so that a portion of all charged airborne particles having a size larger than a predetermined particle size pass through the screening electrode.

4. The sensor according to claim 1, further comprising an optical particle detection unit (380) arranged to optically detect airborne particles in the airflow and to release a measurement signal indicative of the concentration of the optically detected particles.

5. The sensor according to claim 1, further comprising means for removing ozone from the airflow through said passage, which means is located in the passage downstream of the discharge electrode.

6. A sensor according to claim 1, which is operable in a calibration mode, wherein the measured signal of the electric current meter (136, 248) with the discharge electrode (120) being deactivated is used as a zero level for subsequent measurements with the discharge electrode being activated.

7. The sensor according to claim 1, wherein at least one end of the passage is provided with a shielding plate.

8. The sensor according to claim 1, wherein the particle sensing section comprises:
   means (130, 132; 242, 244) for subjecting the airflow to an electric field for inducing electrostatic precipitation of electrically charged airborne particles on a precipitation surface (132; 244); and
   an electric current meter (136) electrically connected to the precipitation surface, for generating a measurement signal indicative of the charge of any electrically charged airborne particles that precipitate on the precipitation surface.

9. The sensor according to claim 8, wherein the means for subjecting the airflow to an electric field comprises at least two parallel conducting electrode elements (130, 132), at least one of which comprises the precipitation surface.

10. The sensor according to claim 8, wherein the means for subjecting the airflow to an electric field is adapted to create an electric field perpendicular to the downstream direction.

11. The sensor according to claim 1, further comprising an evaluation unit capable of receiving the measurement signal or signals, the evaluation unit being adapted to output a signal indicative of at least one in a group comprising:
   a length concentration of airborne particles in the airflow;
   a number concentration of airborne particles with a diameter larger than 10 nm in the airflow;

a number-averaged particle size of airborne particles larger than 10 nm in the airflow; and a concentration of optically-detected airborne particles in the airflow.

12. The sensor according to claim 11, wherein the evaluation unit is capable of calculating from its output signal, in the course of time, a cumulative number that is proportional to either:

an approximate total amount of airborne particles larger than 10 nm, that has precipitated inside the particle sensing section since a predetermined point in time; or an approximate total amount of airborne particles that has been detected by the optical particle detection unit since a predetermined point in time.

13. An air handling system comprising:

a sensor (418) according to any one of the previous claims for providing an output signal indicative of a concentration of airborne particles, an air processing unit (410); and a controller (416) arranged to control the air processing unit on the basis of the output signal of the sensor.

14. A method (500) for sensing airborne particles larger than 10 nm in an air sample in a passage with open ends, the method comprising the steps of:

generating (512) airborne unipolar ions;

applying (514) a first electric field adapted to subject generated airborne ions to an electrostatic force along the passage into a first direction, thereby causing a movement of the air sample in the first direction and charging airborne particles in the air sample;

passing (516) the air sample through an air-pervious counter electrode adapted to remove part of the airborne ions from the air sample;

applying (518) a second electric field adapted to subject remaining airborne ions to an electrostatic force in a second direction, distinct from the first direction, for separating airborne ions from the air sample;

applying (520) a third electric field for precipitating airborne charged particles onto a precipitation surface in the passage; and measuring (522) the charge of the precipitated charged particles on the precipitation surface.

15. The method according to claim 14, further comprising the step of optically detecting (510) airborne particles in the air sample.

* * * * *